United States Patent
Farina et al.

(10) Patent No.: US 7,013,202 B2
(45) Date of Patent: *Mar. 14, 2006

(54) PRECISE POSITION CONTROLLED ACTUATING METHOD AND SYSTEM

(75) Inventors: Dino J. Farina, Holliston, MA (US); Timothy M. Fallon, Somerville, MA (US); Socratis Kalogrianitis, Somerville, MA (US); Peter Taylor, Buellton, CA (US)

(73) Assignee: Image Therm Engineering, Inc., Sudbury, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/826,609

(22) Filed: Apr. 16, 2004

(65) Prior Publication Data

US 2004/0199296 A1    Oct. 7, 2004

Related U.S. Application Data

(63) Continuation of application No. 10/176,930, filed on Jun. 21, 2002, now Pat. No. 6,799,090.

(60) Provisional application No. 60/299,874, filed on Jun. 21, 2001.

(51) Int. Cl.
*G05D 11/00* (2006.01)
(52) U.S. Cl. .................. 700/282; 73/119; 73/865.9
(58) Field of Classification Search ........ 700/282–283; 239/380–381; 73/119 A, 1.05, 865.9, 1.02, 73/1.37, 1.41
See application file for complete search history.

(56) References Cited

U.S. PATENT DOCUMENTS

| | | | |
|---|---|---|---|
| 4,357,670 A | 11/1982 | McFarlane | |
| 4,415,265 A | 11/1983 | Campillo et al. | |
| 4,614,300 A | 9/1986 | Falcoff | |
| 4,965,841 A | 10/1990 | Kaneko et al. | |
| 4,984,158 A * | 1/1991 | Hillsman | 128/200.14 |
| 4,992,952 A | 2/1991 | Sasaki | |

(Continued)

OTHER PUBLICATIONS

Dvorak, P., "How to See Aerosol Spray Patterns and Plumes," *Machine Design*, 72(13): 122 (Jul. 6, 2000).

(Continued)

*Primary Examiner*—Zoila Cabrera
(74) *Attorney, Agent, or Firm*—Hamilton, Brook, Smith & Reynolds, PC

(57) ABSTRACT

A system for actuating a spray pump assembly comprises a reference platform, a motor, a drive transmission, a spray pump holder, a force coupler, a force transducer, and a system controller. The motor receives a power and control input, and produces a rotary drive output. The drive transmission receives the rotary drive output and produces a linear drive output. The spray pump holder secures the spray pump assembly. The force coupler couples the linear drive output to the spray pump, and applies a force to the spray pump. The force transducer produces a force signal proportional to the force applied to the spray pump. The system controller receives a set of test inputs and provides the control input to the motor as a function of the set of test inputs. The system actuates the spray pump mechanism according to an actuation profile defined by the set of test inputs.

24 Claims, 11 Drawing Sheets

U.S. PATENT DOCUMENTS

| | | |
|---|---|---|
| 5,075,014 A | 12/1991 | Sullivan |
| 5,284,133 A * | 2/1994 | Burns et al. ............ 128/200.23 |
| 5,337,926 A | 8/1994 | Drobish et al. |
| RE34,910 E | 4/1995 | Funkenbusch et al. |
| 5,561,527 A | 10/1996 | Krone-Schmidt et al. |
| 5,879,713 A | 3/1999 | Roth et al. |
| 6,029,600 A | 2/2000 | Davis |
| 6,149,071 A | 11/2000 | MacCallumMhor et al. |
| 6,193,936 B1 | 2/2001 | Gardner et al. |
| 6,256,597 B1 | 7/2001 | Wang et al. |
| 6,508,112 B1 | 1/2003 | Verhoeven |
| 6,665,421 B1 | 12/2003 | Farina |

OTHER PUBLICATIONS

Badreldin, Amira M., "Real-Time Analysis of Fuel Spray Images," *IEEE*, pp. 622-624 (1987).

Lopera, J. F. G., et al., "Improved Entropic Edge-Detection." Paper supported by grant MAR97-0464-C04-02 of Spanish Government. No date given.

Pastor, J. V., et al., "Analysis Methodology of Diesel Spray and Flame by Means of In-Cylinder Endoscopic Imaging," (The Institution of Electrical Engineers), Savoy Place, London: IEE (2000).

* cited by examiner

PRECISE POSITION CONTROLLED ACTUATING METHOD AND SYSTEM

RELATED APPLICATIONS

This application is a continuation of U.S. application Ser. No. 10/176,930, filed Jun. 21, 2002 now U.S. Pat. No. 6,799,090 which claims the benefit of U.S. Provisional Application No. 60/299,874, filed Jun. 21, 2001. The entire teachings of the above application are incorporated herein by reference.

BACKGROUND OF THE INVENTION

The present invention relates to electromechanical actuators, and more particularly, to devices for providing precisely controlled actuation of spray pump mechanisms.

The US Food and Drug Administration (FDA) strongly recommends automated actuation of nasal spray devices subject to in-vitro bioequivalence testing to decrease variability in drug delivery due to operator factors (including removal of potential analyst bias in actuation) and increase the sensitivity for detecting potential differences between drug products. The FDA further recommends that an automated actuation system have settings or controls for actuation force, length of stroke, actuation velocity, hold time, return time, delay time between successive actuations, and actuation number. Selection of appropriate settings should be relevant to proper usage of the nasal aerosol or nasal spray by the trained patient, and should be documented based on exploratory studies in which actuation force, actuation time, and other relevant parameters are varied. One such study includes "Guidance for Industry: Bioavailability and Bioequivalence Studies for Nasal Aerosols and Nasal Sprays for Local Action," by Wallace P. Adams, U.S. Department of Health and Human Services, Food and Drug Administration, Center for Drug Evaluation and Research (CDER), June 1999.

Thorough characterization of the spray pump's performance in terms of its emitted spray pattern, plume geometry and/or droplet size distribution are known to be affected by the means in which the spray pump is actuated. For example, slow actuation will likely cause poor atomization, producing a stream-like flow. Fast actuation will likely cause too fine a spray to be produced, leading to poor absorption in the nasal mucosa and unwanted inhalation and deposition of the droplets in the throat and lungs.

From a mechanical perspective, over-actuation (forcing the spray pump assembly beyond its intended stopping point) of the spray pump device must be avoided. If the spray pump mechanism is over-actuated, permanent deformations can occur to the delicate pump orifice, swirl chambers and/or closure mechanisms, all of which can manifest themselves in higher than expected variability in the pump's spray performance and flow characteristics. Further, rigidly holding the nozzle of the spray pump in place during actuation is vital to ensure that the spray develops properly and exits the nozzle normally so that measurements of spray pattern, plume geometry and droplet size distribution are not artificially biased due to unwanted movement of the nozzle.

The Innova Systems (Pennsauken, N.J.) Nasal Spray Pump Actuators (NSP and eNSP) are prior art automated nasal spray actuators. Both models use the same operating principle: a pneumatic cylinder connected to a solid plate (contact plate) is used to compress the spray pump against a spring loaded holding plate and clip mechanism. Typically, these actuators are connected to a compressed air source and a computer interface to allow a user to set the actuation force, contact force, holding time, and dose time for the actuation event. In operation, these actuators adjust an air pressure regulator so that the pneumatic cylinder will first apply the prescribed contact force to the bottom side of the spray pump. Presumably, this application of the contact force is done to minimize the time delay in producing the spray and/or to prevent the compression plate from striking the spray pump with a dynamic load, which could damage the pump due to the high dynamic forces achievable in the system. Next, the pressure regulator is adjusted again so that the pneumatic cylinder applies the prescribed actuation force (typically higher than the contact force). This action compresses the spray pump at a rate determined by the pneumatic efficiency of the system and the mechanical spring resistance of the spray pump and fluid combination. The compression rate cannot be controlled. As a result, once the pressure regulator is set, the contact plate will move at a rate determined by the system, not the user.

Experience with using these actuators has shown the following difficulties and shortcomings:

1. Lack of position and velocity controls leads to uncontrolled, "air hammer"—like performance with substantial spray pump over-actuation. This phenomenon has led to measurable degradation in spray pump performance over time and larger than expected variations in delivered dosage content. These problems are likely due to progressive deterioration in the moving pump components due to over-actuation.

2. Lack of a nozzle holding mechanism leads to unwanted movements of the nozzle during actuation. This causes artificial distortions and substantial variability to appear in the associated spray pattern and plume geometry test data.

3. Difficulties associated with pneumatic control lead to oscillating contact force application and this leads to pre-spray droplets forming on the nozzle tip and measurable variability in spray pattern, plume geometry, and droplet size distribution data.

4. Reliance on variable quality, laboratory compressed air sources leads to inconsistent actuation performance and potential safety issues.

5. Uncertain actuation event-time triggering causes difficulty in acquiring time critical spray data such as spray pattern and plume geometry.

6. Uncertain applied force measurements do not give a user confidence that the actuator is applying the desired force to the spray pump.

7. Absence of recordable applied force and/or position/velocity data make it difficult to chronicle the actuation event history.

SUMMARY OF THE INVENTION

In one aspect, a system for actuating a spray pump assembly including a reservoir component and a pump/nozzle component comprises a reference platform, a motor component, a drive transmission component, a spray pump holder component, a force coupler, a force transducer, and a system controller. The reference platform provides a foundation upon which the components of the system are mounted. The motor component is fixedly attached to the reference platform, receives a power input and a control input, and produces a rotary drive output therefrom. The drive transmission component is fixedly attached to the reference platform, receives the rotary drive output and produces a linear drive output therefrom. The spray pump holder component is removably attached to the reference platform, and removably secures the spray pump assembly. The force coupler couples the linear drive output to the spray pump mechanism, so as to apply a force to the spray pump mechanism. The force transducer produces a force signal proportional to the force applied to the spray pump mechanism. The system controller receives a set of test inputs including (i) the force signal, (ii) one or more feedback signals from the motor component, and (iii) user input corresponding to spray pump test parameters. The system controller provides the control input to the motor component as a predetermined function of the set of test inputs. The system is operative to actuate the spray pump mechanism according to an actuation profile defined by the set of test inputs.

In one embodiment, the motor component includes a servomotor. In another embodiment, the servomotor includes a motor controller for receiving and processing the control input and for providing the one or more feedback signals, and for storing the actuation profile. The servomotor includes an encoder for monitoring the angular position of the rotary drive output and for producing an angular position signal corresponding to the angular position of the rotary drive output. The servomotor further includes a driver for receiving the actuation profile from the motor controller and the power input, and for producing a drive signal therefrom. The servomotor also includes an electric rotary motor for receiving the drive signal and for producing the rotary drive output therefrom.

In another embodiment, the motor component includes any one of a variety of stepper motors known in the art.

In another embodiment, the actuation profile includes a quiescent position of the spray pump mechanism.

In another embodiment, the actuation profile includes a fully actuated position of the spray pump assembly.

In another embodiment, the actuation profile includes a velocity profile from a quiescent position of the spray pump assembly to a fully actuated position of the spray pump mechanism.

In another embodiment, the velocity profile includes velocity with respect to time.

In another embodiment, the actuation profile includes a force profile from a quiescent position of the spray pump mechanism to a fully actuated position of the spray pump mechanism.

In another embodiment, the force profile includes force with respect to time.

In another embodiment, the actuation profile includes a hold time parameter corresponding to an amount of time the spray pump assembly is held in a fully actuated position.

In another embodiment, the drive transmission component includes at least one linear screw-rail assembly.

In another embodiment, the at least one linear screw-rail assembly includes an anti-backlash linear screw-rail assembly.

In another embodiment, the at least one linear screw-rail assembly includes a low friction coating on at least a screw component within the linear screw-rail assembly.

In another embodiment, the low friction coating includes a Teflon-based material.

In another embodiment, the at least one linear screw-rail assembly includes ball bearing supports for supporting a screw component within the linear screw-rail assembly.

Another embodiment further includes a first pulley fixedly attached to the rotary drive output, a second pulley fixedly attached to a screw component within the linear screw-rail assembly, and a drive belt for coupling the first pulley to the second pulley.

In another embodiment, the first pulley and the second pulley each include a plurality of teeth, and the drive belt includes a plurality of ribs, such that in operation the teeth on the first pulley and the teeth on the second pulley mesh with the ribs on the drive belt.

In another embodiment, the rotary drive output is directly coupled to the drive transmission component.

In another embodiment, the spray pump holder component removably secures the pump/nozzle component, and the coupler couples the linear drive output to the reservoir component.

In another embodiment, the spray pump holder component removably secures the reservoir component, and the coupler couples the linear drive output to the pump/nozzle component.

In another embodiment, the force transducer is disposed between the spray pump assembly and linear drive output.

In another embodiment, the force transducer is disposed between the spray pump assembly and the spray pump holder component.

In another embodiment, the force transducer is disposed between the spray pump holder and the reference platform.

In another embodiment, the system controller includes a digital acquisition assembly for sampling an angular position signal that characterizes the angular position of the rotary drive output, so as to generate one or more digital samples corresponding to the angular position signal. The system controller further includes a computer system that receives the set of test inputs and the one or more digital samples, generates the actuation profile and provides the actuation profile to the motor component. The computer system also receives the one or more feedback signals from the motor component and recording one or more physical parameters of the spray pump assembly during actuation.

In another embodiment, the one or more physical parameters of the spray pump assembly includes a position versus time profile that describes the position of the nozzle pump component with respect to the reservoir component as a function of time.

In another embodiment, the one or more physical parameters of the spray pump assembly includes a force versus time profile that describes force applied to the nozzle pump component with respect to the reservoir component as a function of time.

In another embodiment, the computer system performs a calibration procedure, calculates one or more compensation values, and uses the compensation values to modify the one or more physical parameters.

In another embodiment, the computer system performs a calibration procedure, calculates one or more compensation values, and uses the compensation values to modify the control input to the motor component.

In another embodiment, the system controller generates an actuation profile representative of a human hand actuating the spray pump assembly.

In another aspect, a method of actuating a spray pump via an actuator system comprises removably securing the spray pump assembly to a spray pump holder component. The method further comprises determining (i) a quiescent position of the spray pump, and (ii) a fully actuated position of the spray pump assembly. The method further comprises generating an actuation profile as a predetermined function of the quiescent position, the fully actuated position, and user input corresponding to spray pump test parameters. The method also comprises actuating the spray pump according to the actuation profile. The actuator system includes a rotary motor driving a linear screw-rail assembly, thereby applying a force to the spray pump assembly.

In another embodiment, the step of determining the quiescent position of the spray pump further includes measuring an amount of force applied to the spray pump assembly, and advancing the linear screw rail assembly until the amount of force applied to the spray pump assembly exceeds a first predetermined value. The step of determining the quiescent position of the spray pump assembly also includes recording a position of the linear screw rail assembly when the amount of force applied to the spray pump assembly exceeds the first predetermined value.

In another embodiment, the step of determining the fully actuated position of the spray pump assembly further includes continuing to advance the linear screw rail assembly until the amount of force applied to the spray pump assembly exceeds a second predetermined value. The step of determining the fully actuated position of the spray pump assembly also includes recording a position of the linear screw rail assembly when the amount of force applied to the spray pump assembly exceeds the second predetermined value.

In another aspect, a spray pump holder for securing a spray pump assembly includes a clamp having an aperture disposed about a central axis, and a plurality of fingers disposed about the perimeter of the aperture and extending out from the clamp parallel to the central axis. The spray pump holder also includes a compression member removably attached to the clamp. The pump/nozzle component is inserted into the aperture along the central axis, and the compression member, when attached to the clamp, compresses the plurality of fingers against the pump/nozzle component so as to secure the pump/nozzle component to the clamp.

In another embodiment, the clamp consists of a low friction material. In one embodiment, the low friction material is Teflon.

In another embodiment, the compression member is constructed and arranged so as to variably compress the plurality of fingers against the pump/nozzle component.

In another embodiment, the clamp and the compression member include mating threads, such that the compression member screws into the clamp and drives the fingers toward the central axis. In one embodiment, the compression member consists of anodized aluminum.

Another embodiment of the spray pump holder further includes an annular insert disposed about the central axis, between the fingers and the central axis. The pump/nozzle component is inserted through the annular insert and the fingers compress the annular insert against the pump/nozzle component. In another embodiment, each of the fingers is characterized by a triangular cross section in a plane perpendicular to the central axis.

In another embodiment, the clamp is characterized by a substantially square body, disposed within a plane that is perpendicular to the central axis. In another embodiment, opposite sides of the square body slide into, or otherwise engage, corresponding grooves in a reference platform.

In another aspect, a spray pump holder for securing a spray pump assembly comprises a bracket for supporting the spray pump assembly, and at least one securing strap for removably securing the spray pump assembly against the bracket.

In another embodiment, the bracket includes a first cradle member having a first engaging surface for retaining a first surface of the reservoir component, and a second cradle member having a second engaging surface for retaining a second surface of the reservoir component.

In another embodiment, the first engaging surface is substantially orthogonal to the second engaging surface.

In another embodiment, the first engaging surface includes a V-shaped surface, so that the first engaging surface contacts a reservoir component having an arcuate exterior surface at two locations.

In another embodiment, the second engaging surface includes a V-shaped surface, so that the second engaging surface contacts a reservoir component having an arcuate exterior surface at two locations.

In another embodiment, the bracket further includes an aperture, disposed between the first cradle member and the second cradle member, for accommodating a heel portion of the spray pump assembly.

Another embodiment of the spray pump holder further includes a first securing strap and a second securing strap. The first securing strap secures the spray pump assembly against the first cradle member, and the second securing strap secures the heel portion of the spray pump assembly into the aperture and against the second cradle member. In one embodiment of the spray pump holder, a first end of the at least one securing strap is fixedly attached to a first anchor on the bracket, and a second end of the at least one securing strap is removably attached to a second anchor on the bracket.

In another embodiment, the second end of the at least one securing strap loops around the second anchor removably attaches to a distal portion of the securing strap.

In another aspect, a spray pump holder for securing a spray pump assembly comprises a base including a body member, and a housing member having a stop tab. The spray pump holder further includes a clamping assembly including a first lever and a second lever pivotally attached at a pivot point about a pivot axle. The spray pump holder also includes a spring attached to the first lever and the second lever so as to force together a first end of the first lever and a first end of the second lever. The stop tab provides a platform or buttress, against which a pump/nozzle component of a spray pump assembly presses, and the pump/nozzle component is secured between the first end of the first lever and a first end of the second lever.

In another embodiment, the body member is characterized by a square body, and opposite sides of the square body slide into corresponding grooves in a reference platform.

BRIEF DESCRIPTION OF DRAWINGS

The foregoing and other objects of this invention, the various features thereof, as well as the invention itself, may be more fully understood from the following description, when read together with the accompanying drawings in which.

DETAILED DESCRIPTION OF THE INVENTION

Figure 1:
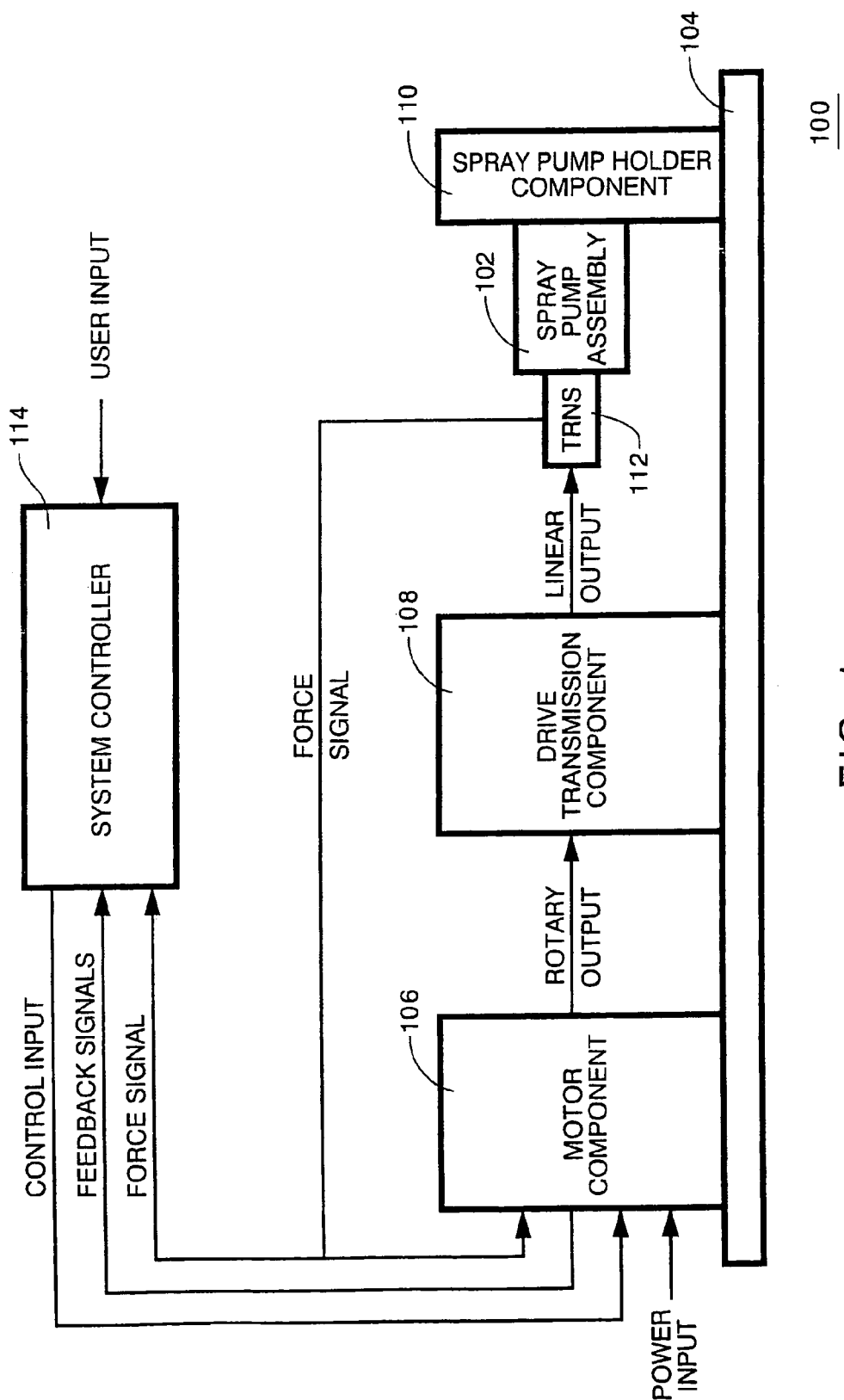
FIG. 1 shows a block diagram view of one preferred embodiment of a system for providing precisely controlled actuation of spray pump assembly.

FIG. 1 shows a block diagram view of one preferred embodiment of a system 100 for providing precisely controlled actuation of spray pump assembly 102. The system includes a reference platform 104, a motor component 106, a drive transmission component 108, a spray pump holder component 110, a force transducer 112, and a system controller 114. The reference platform 104 provides a substantially rigid platform upon which the various components of the system 100 may be mounted, and provides a fixed reference from which the other components may relate to one another.

Figure 2B:
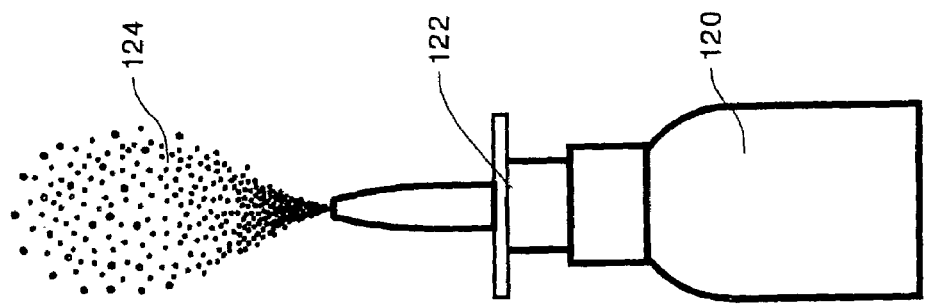
FIG. 2B shows a nasal spray pump assembly in the fully actuated position.
Figure 2A:
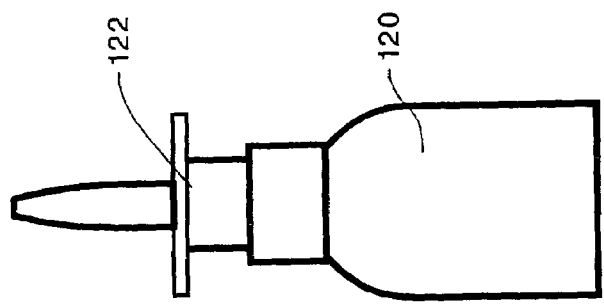
FIG. 2A shows a nasal spray pump assembly in the quiescent position.
Figure 2D:
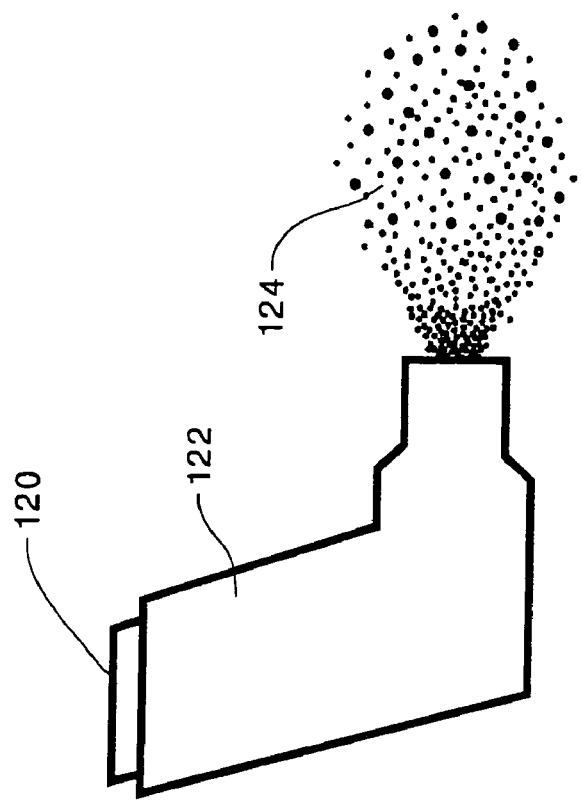
FIG. 2D shows an MDI spray pump assembly in the fully actuated position.
Figure 2C:
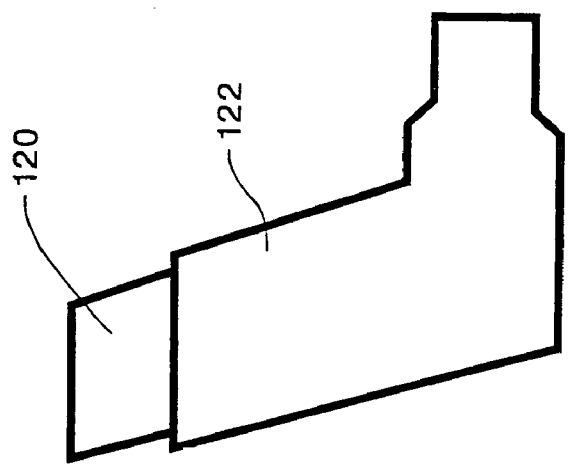
FIG. 2C shows an MDI spray pump assembly in the quiescent position.

In general, the spray pump assembly 102 consists of two cooperative components, and emits a spray plume when an applied force moves the two cooperative components relative to one another. In one embodiment the spray pump assembly 102 includes a reservoir component 120 and a pump/nozzle component 122, as shown in FIG. 2A and FIG. 2B. FIG. 2A shows the spray pump assembly 102 in the quiescent position, and FIG. 2B shows the spray pump assembly 102 in the fully actuated position. The spray pump assembly shown in FIGS. 2A and 2B is generally known in the art as a nasal spray pump assembly. The nasal spray pump emits a spray plume 124 when the assembly transitions from the quiescent position to the fully actuated position, and automatically returns to the quiescent position. Another embodiment of the system 100 may be used to actuate another type of spray pump assembly generally known as a metered dose inhaler (referred to herein as "MDI"), as shown in FIGS. 2C and 2D. Although the mechanics of the nasal spray pump assembly and the MDI differ significantly, the two cooperative components of the MDI will be referred to herein as the reservoir component 120 and the pump/nozzle component 122 as shown in FIGS. 2C and 2D for explanatory purposes only. Thus, FIG. 2C shows the spray pump assembly 102 in the quiescent position, and FIG. 2D shows the spray pump assembly 102 in the fully actuated position. The MDI emits a spray plume 124 when the assembly transitions from the quiescent position to the fully actuated position, and automatically returns to the quiescent position.

The motor component 106 is mounted to the reference platform 104, receives a power input from an external power source (not shown) and a control input from the system controller 114, and produces a rotary drive output dependent on the power and control inputs. In one embodiment, the rotary drive output consists of a cylindrical shaft rotating about an axis of rotation, and may be instantaneously characterized by an angular position, an angular velocity, an angular acceleration and a torque. The rotary drive output may include rotation in either direction (i.e., clockwise or counterclockwise), and may include an angular velocity of zero (i.e., at rest—not rotating).

The drive transmission component 108 is also mounted to the reference platform 104 and receives the rotary drive output from the motor component 106. The drive transmission component 108 transforms the rotational motion of the rotary drive output into linear motion, so as to produce a linear drive output. In one embodiment, the linear drive output consists of a shaft traveling along a linear axis. In another embodiment, the linear drive output consists of a nut assembly traveling on a screw-rail along a linear axis. The linear drive output may be instantaneously characterized by a linear position, a linear velocity, a linear acceleration and a linear force. The linear drive output may include translation in either direction along the linear axis, and may include a linear velocity of zero (i.e., at rest—not moving).

The spray pump holder 110 is removably attached to the reference platform 104 so that the spray pump holder 110 is held stationary with respect to the reference platform 104 during system operation, but can be removed and repositioned with relative ease (i.e., without special tools or significant effort). The spray pump holder 110 is attached to the reference platform 104 using any of a variety of techniques known in the art, including but not limited to a friction engagement (e.g., press fit), a threaded engagement (e.g., screw threads into a tapped aperture), a keyed latch fit, etc. Similarly, the spray pump holder 110 removably secures the spray pump assembly 102. During operation, the spray pump assembly 102 is held stationary with respect to the reference platform 104 during system operation, but can be removed and repositioned, or swapped with an alternate spray pump assembly with relative ease.

The linear drive output from the drive transmission component 108 is coupled to the spray pump assembly 102 via a "force coupler," so that during operation, the linear drive output applies a force to the spray pump assembly 102. In one embodiment, this force coupler consists of a direct physical connection between the linear drive output and the spray pump assembly 102. In other embodiments, the coupling includes a linkage between the linear drive output and the spray pump assembly 102, such as a mechanical linkage, pneumatic linkage, hydraulic linkage, or other similar linkage, to redirect or otherwise condition the linear drive output.

The force transducer 112 produces a force signal that is proportional to the amount of force delivered to the spray pump assembly 102, and provides the force signal to the system controller 114 and the motor component 106. The motor component 106 uses the force signal to detect destructive force levels on the spray pump assembly 102. The motor component 106 compares the force signal to a predetermined threshold value, and reduces or eliminates the forces prior to damaging the spray pump assembly 102. In the embodiment shown in FIG. 1, the force transducer 112 is situated between the linear drive output and the spray pump assembly 102. Other embodiments of the system 100 may incorporate the force transducer 112 between the spray pump assembly 102 and the spray pump holder 110, or between the spray pump holder 110 and the reference platform. In general, the force transducer 112 may be situated anywhere that results in a force signal that is proportional to the amount of force delivered to the spray pump assembly 102.

The system controller 114 is electrically coupled to the motor component 106 and the force transducer 112. The system controller 114 receives the force signal from the force transducer 112 and feedback signals from the motor component 106. Among other data, the feedback signals from the motor component 106 provide information to the system controller 114 regarding the angular position of the rotary drive output. The system controller 114 also receives user input data that in part defines the desired actuation profile to which the spray pump assembly is to be subjected. The actuation profile includes, but is not limited to, actuation velocity, actuation acceleration, initial actuation delay, actuation hold time, post-actuation delay, number of iterative actuations, among others. Further, one unique actuation profile may be used for the upstroke (i.e., from quiescent position to fully-actuated position) and another unique actuation profile for the down-stroke (i.e., from the fully-actuated position to the quiescent position). The system controller 114 also measures and records a plurality of pump stroke statistics, including, but not limited to, distance required to achieve maximum velocity, distance at maximum velocity, distance required to stop from maximum velocity, time required to achieve maximum velocity, time spent while at maximum velocity, time required to stop from maximum velocity, time required to reach the fully-actuated position, total time required for overall actuation, among others.

Figure 3A:
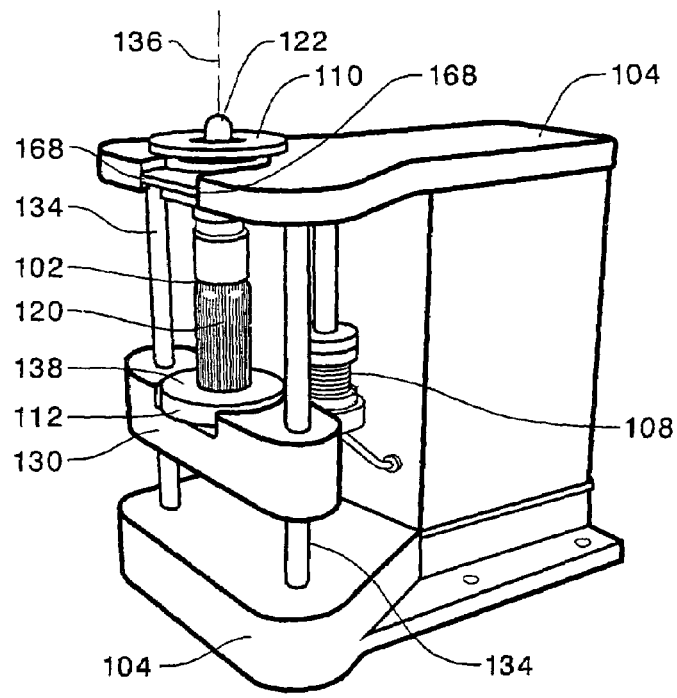
FIG. 3A shows a perspective view of one embodiment of the actuator system.
Figure 3B:
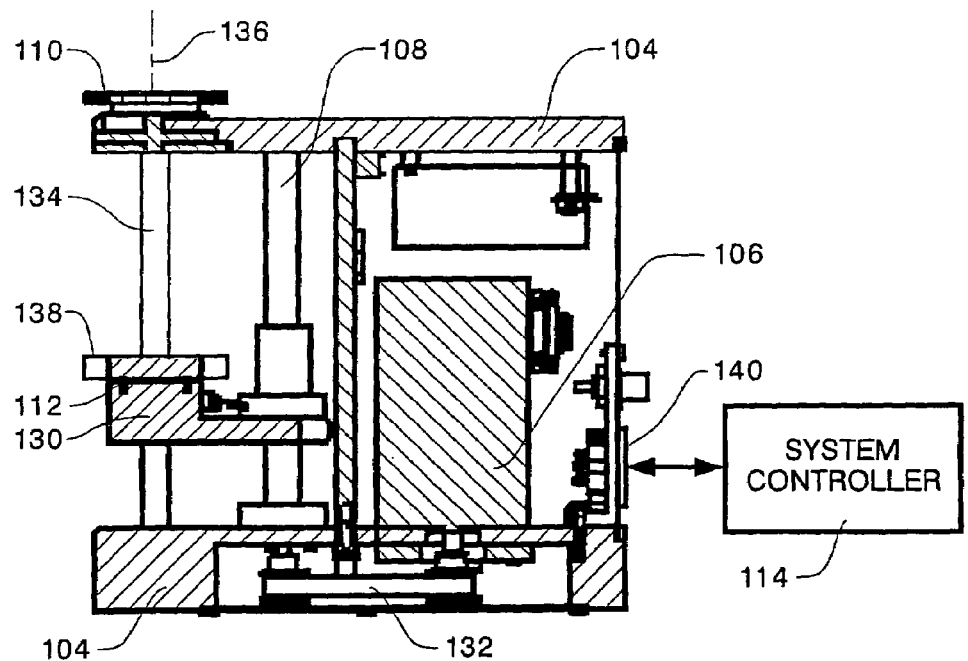
FIG. 3B is a sectional view of the system of FIG. 3A.
Figure 3C:
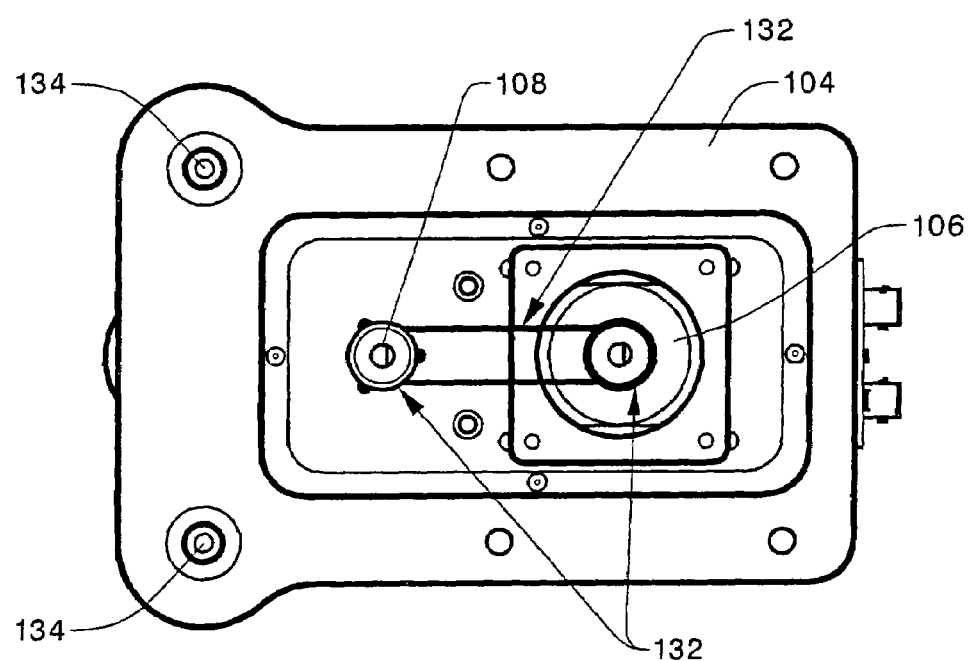
FIG. 3C is a bottom view of the system of FIG. 3A.

Another embodiment of the system 100 described in FIG. 1 is shown in FIGS. 3A, 3B and 3C. FIG. 3A shows a perspective view of the system 100 (without the system controller 114), FIG. 3B is a sectional view of the system 100, showing internal components hidden by the shroud 138 in FIG. 3A, and FIG. 3C is a bottom view of the system 100. This embodiment includes a reference platform 104, a motor component 106, a drive transmission component 108 (also referred to in this embodiment as a "linear screw-rail assembly"), a spray pump holder component 110, a force transducer 112, a force coupler 130 (also referred to in this embodiment as a "compression plate"), a drive coupler 132, two guide rods 134, and system controller 114. The interaction of these components is the same as for similarly numbered components in FIG. 1; however, this embodiment includes several components not shown in FIG. 1. The compression plate 130 couples the force generated by the linear drive output to the spray pump assembly 102. The compression plate 130 travels along two guide rods 134 that are fixedly attached to the reference platform 104 and are parallel to the spray axis 136. Thus, the direction of travel of the compression plate 130 is parallel to the spray axis 136. The drive coupler 132 includes two pulleys and a drive belt. One of the pulleys is fixedly attached to the rotary drive output of the motor component 106 (i.e., the motor spindle), so that the pulley rotates along with the motor spindle. The other pulley is fixedly attached to the screw-rail spindle of the linear screw-rail assembly 108, so that the pulley rotates along with the screw-rail spindle. The drive belt couples the two pulleys so that the two pulleys rotate synchronously. In one embodiment, the pulleys have teeth or similar frictional ribs that correspond to teeth or frictional ribs on the drive belt, so that in operation the drive belt meshes with the pulleys to reduce or prevent slippage. In other embodiments, the drive coupler 132 may include gears rather than pulleys, and a drive chain rather than a drive belt, or other similar techniques known in the art for coupling rotational motion.

Figure 4A:
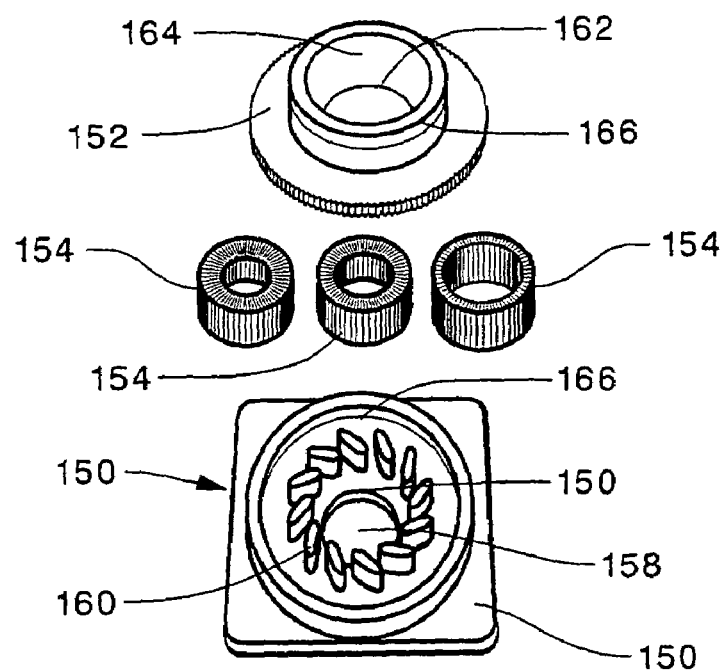
FIG. 4A shows the constituent pieces of the spray pump holder component of the embodiment shown in FIG. 3A.
Figure 4B:
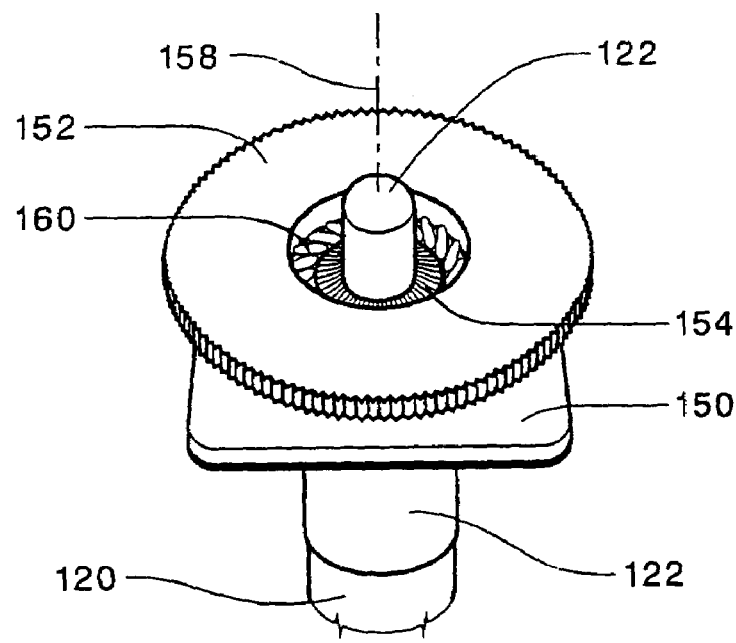
FIG. 4B shows a perspective view of the assembled spray pump holder component secured to a spray pump assembly of FIG. 3A.

FIG. 4A shows the constituent pieces of the spray pump holder component 110 of the embodiment shown in FIG. 3A, including a clamp 150, a compression member 152, and several annular inserts 154. FIG. 4B shows a perspective view of the assembled spray pump holder component 110 secured to a spray pump assembly 102. The clamp 150 includes a square body 155, and an aperture 156 disposed about a central axis 158, through which the pump/nozzle component of the spray pump assembly is inserted. The clamp 150 also includes a plurality of fingers 160 disposed about the perimeter of the aperture 156. The fingers 160 are characterized by a triangular cross-section in the plane perpendicular to the central axis, and extend out from the clamp 150 in a direction parallel to the central axis 158, as shown in FIG. 4. In one embodiment, the clamp 150 is made of Teflon, although other similar low-friction materials (e.g., plastic, composite materials, or a rigid material coated with a low-friction material) may also be used. The compression member 152 includes a disc-shaped body having an aperture 162 arranged such that an interior surface 164 of the compression member 152 is slightly conical. In one embodiment the compression member 152 is made of anodized aluminum, although other similar materials (e.g., plastic, steel, and other rigid metals and composite materials) may also be used. The compression member 152 engages the clamp 150 via mating threads 166, so that the compression member 152 can be screwed into the clamp 150. As the compression member 152 so engages the clamp 150, the interior conical surface 164 of the compression member 152 compresses the fingers 160 inward toward central axis 158 and against the pump/nozzle component. In one embodiment, the spray pump holder component 110 also includes an annular insert 154 disposed about the central axis 158 between the fingers 160 and the central axis 158, so that the pump/nozzle component is inserted through the annular insert 154. In operation, the fingers 160 compress the annular insert 154 against the pump/nozzle component. The square body 155 of the spray pump holder component 110 is inserted into mating grooves 168 in the reference platform 104 (see FIG. 3A). The entire holder/spray pump assembly can thus be rotated along the spray axis in 90 degree increments to allow different orientations of the emitted spray to be viewed by associated spray characterization equipment.

In operation, a spray pump assembly 102 is inserted into the spray pump holder component 110 and placed in the chassis so that the movement of the pump compression plate 130 is in line with the spray axis 136 of the spray pump assembly 102. The compression plate 130 moves along the guide rods 134 in the direction of the spray axis 136, driven by the rotation of the coupled motor and linear screw-rail spindles. The spray pump holder component 110 holds the pump/nozzle component 122 stationary with respect to the reference platform 104, and the compression plate 130 moves the reservoir component 120 with respect to the pump/nozzle component 122 to actuate the spray pump assembly 102.

The force transducer 112 is mounted within the compression plate 130 to measure the force applied to the pump by the movement of the compression plate 130. One embodiment includes a separate contact plate 138, situated over the force transducer 112, that makes contact with the spray pump assembly 102 during actuation. In such embodiments the force transducer 112 is "sandwiched" between the contact plate and the compression plate 130. In addition, the pump contact plate of the present invention is bolted to the top face of the force transducer. This subassembly is bolted halfway between the bearing mounts from below on the compression plate. This arrangement positions the force transducer directly in-line with the direction of applied force, while accurately sandwiching the transducer between the compression plate and pump contact plate for optimal performance.

In the embodiment of FIGS. 3A and 3B, the motor component 106, the linear screw-rail assembly 108 and the two guide rods 134 are mounted perpendicular to the reference platform 104 so that their spindles are parallel to one another. The cross-sections of the rotating spindle of the motor component 106, the screw-rail spindle of the linear screw-rail assembly 108 and the two guide rods 134 in the plane of the reference platform 104 form a "Y" pattern. The motor spindle is positioned at the bottom of the "Y," the screw-rail spindle is positioned at the fulcrum of the "Y," and the two guide rods 134 are positioned at the opposite ends of the "Y" fork.

The embodiment of FIGS. 3A and 3B includes a serial data port 140 for facilitating the transfer of user data corresponding to spray pump test parameters (e.g., programming instructions) from the system controller 114 to the motor component 106. The serial port 140 further facilitates the transfer of feedback signals (e.g., status and motor shaft angular position information) from the motor component 106 to the system controller 112.

In the embodiment of FIGS. 3A and 3B, the system controller 114 includes a data acquisition assembly (referred to herein as a "DAQ") and a computer system. The DAQ receives and samples the angular position signal from the motor assembly 106 and to generate a series of digital samples corresponding to the angular position signal of the motor shaft. The DAQ is operated by control software resident in the computer system, and is primarily used to acquire and synchronize position data from the motor and force data from the force transducer 112. The computer system receives the user data corresponding to the spray pump test parameters and the signals from the DAQ. The computer system also generates an actuation profile from the user data, and provides the actuation profile to the motor component 106 via the serial port 140. The computer system also receives feedback signals from the motor component 106 and the force signal from the force transducer 112, and from these signals determines and records various physical parameters related to the spray pump assembly during the actuation event.

The Quicksilver Controls (Covina, Calif.) QCI-17-3 is an example of a programmable motor assembly suitable for use as the motor component 106 in FIG. 3A. This motor assembly has an integrated digital signal processor (DSP), a 4000-line optical encoder, and drive electronics. The DSP of this motor is capable of interpreting and executing programming commands that are used to digitally set the position, velocity and acceleration of the motor spindle while operating in closed-loop feedback control with continuous input of the angular position signal from the optical encoder. In addition, the DSP of this motor is capable of executing commands and altering the position and/or velocity of the spindle every time a line on the optical encoder is detected, or 4000 times per revolution (120 microseconds). The angular position signal from this optical encoder is compatible with the DAQ described herein.

The Kerk Motion (Hollis, N.H.) SRZ3DU4025T is an example of a linear screw-rail assembly suitable for use as a drive transmission component 108 of FIG. 3A. This linear screw-rail assembly has a Teflon-coated lead screw and slide mechanism and ball bearing supports to reduce friction. In addition, this assembly incorporates a spring-loaded, anti-backlash power nut design to provide positive engagement between the threads on the lead screw and power nut drive mechanisms in both forward and backward movements.

The Sensotec (Columbus, Ohio) 31 is an example of a force transducer suitable for use as the force transducer 112 of FIG. 3A. This force transducer has a sensitivity range of 0 to 50 pounds of force. In addition, when coupled with the UV signal conditioner also from Sensotec, it forms an integrated sensor package with high-level voltage signal outputs compatible with the DAQ described herein.

The York Industries (Garden City Park, N.Y.) 172-2GT-09 and 22-2GT09-1A-3/16 are an example of a drive belt and pulley combination, respectively, suitable for use as the drive coupler 132 of FIG. 3A. This pulley and belt combination is designed to mesh with one another to minimize slip between the drive spindles on the motor and linear screw-rail assemblies.

The National Instruments Corporation (Austin, Tex.) PCI-6023E is an example of a DAQ suitable for use as the DAQ described herein for the system controller 114 of FIG. 3A. This DAQ board can simultaneously sample and synchronize the angular position signal from the optical encoder of the electric motor assembly and the force signal from the force transducer 112. In addition, this DAQ board is designed to operate in a standard personal computer.

The Dell Computer Corporation (Round Rock, Tex.) Dimension XPS R400 is an example of a computer system suitable for use as part of the system controller 114 of FIG. 3A. The serial port of this computer system provides a communications interface compatible with the DSP of the motor component 106. In addition, this computer system is compatible with PCI-6023E DAQ and the control software described herein.

The control software written for and executed by the computer system in the system controller 114 is designed to perform the following functions:

1. Verify the proper operation of the motor, force transducer and DAQ board, in addition to diagnostic checks of other system components.

2. Step the user through calibration procedures, calculates calibration constants and incorporates those calibration constants into the system.

3. Automatically characterizes the spray pump assembly by determining the length of stroke and spray pump assembly bottom position (i.e., quiescent position).

4. Allow a user to specify the actuation profile in terms of velocity, acceleration and hold time, among other parameters.

5. Allow the user to specify the event triggering mode as either internal (i.e., controlled by the software) or external to the system (i.e., slaved to an external trigger source).

Figure 5A:
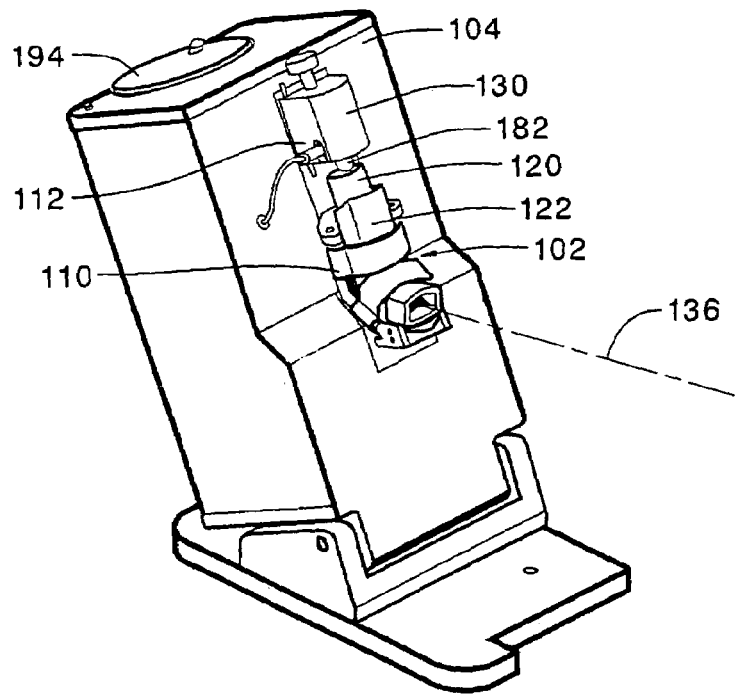
FIG. 5A is a perspective view of an MDI spray pump actuator.
Figure 5B:
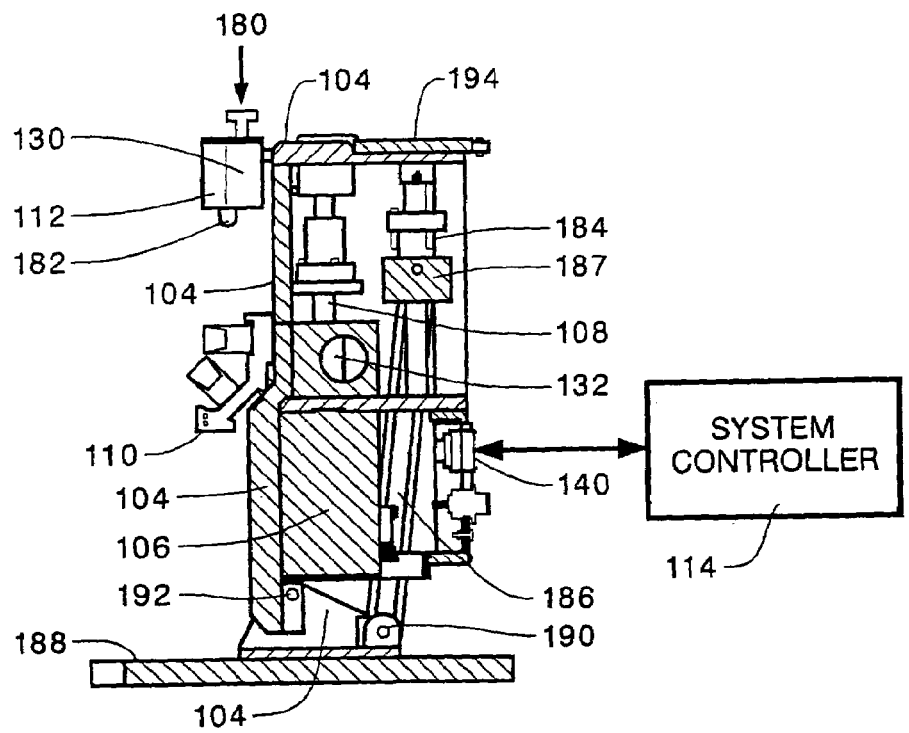
FIG. 5B is a side sectional view of the embodiment of FIG. 5A.

Another embodiment of the invention, used to actuate MDI assemblies, is shown in FIGS. 5A and 5B. FIG. 5A is a perspective view of this embodiment, and FIG. 5B is a side sectional view of this embodiment. In this embodiment, the spray pump holder 110 secures the pump/nozzle component 122 of the spray pump assembly 102 (i.e., the MDI assembly) to the reference platform 104 as shown. Refer to FIGS. 2C and 2D for the constituent components of the MDI type of spray pump assembly. In operation, the force coupler 130 moves in a downward motion (i.e., in the direction of the arrow 180 in FIG. 5B) to actuate the spray pump assembly 102. A compression finger 182, analogous to the contact plate 138 in the embodiment of FIG. 3A, makes contact with the reservoir component 120 of the spray pump assembly and applies the actuating force. FIG. 5B shows the motor component 106 directly coupled to the drive transmission component 108 (a single linear screw-rail assembly in this embodiment) via a direct drive coupling 132, in contrast to the pulley and belt drive coupling of the FIG. 3A embodiment. The embodiment shown in FIGS. 5A and 5B includes a second linear screw-rail assembly 184 that operates in conjunction with a tilt rail 186 to tilt the upper portion of the actuator system with respect to the base member 188. The second linear screw-rail assembly 184 is attached to the reference platform 104. A first end of the tilt rail 186 is pivotally attached to the nut component 187 of the linear screw-rail assembly 184, and the second end of the tilt rail 186 is pivotally attached to a pivot point 190 on the base member 188. As the nut component 187 translates along the screw rail portion of the screw rail assembly 184, the tilt rail 186 forces the upper portion of the actuator system to pivot on a second pivot point 192 on the base member 188. A positioning knob 194 on the top surface of the upper portion of the actuator system is mechanically coupled to the second linear screw-rail assembly 184. As the positioning knob 194 is turned, the nut component 187 travels linearly along the screw rail assembly 184.

For use in spray plume imaging systems, ideally the spray axis 136 from the spray pump assembly 102 is parallel to the base member 188, i.e., the spray axis 136 exactly horizontal to the working surface upon which the system sits. Since MDI spray pump assemblies are not manufactured to any standard form factor, the embodiment shown in FIGS. 5A and 5B can be adjusted, via the positioning knob 194, the second linear screw rail assembly 184 and the tilt rail 186, until the spray axis 136 is parallel to the base member 188. Thus, in general, the positioning knob 194, the second linear screw rail assembly 184 and the tilt rail 186 may be used to adjust the angle of the spray axis 136 with respect to an external reference plane. Other techniques known in the art may also be used to adjust the spray axis 136. For example, a simple arcuate sliding bracket with a locking nut may be used to tilt the system with respect to the working surface, or an external tilting platform may be interposed between the actuating system and the working surface to vary the attitude of the spray axis 136. Further, the angle of the spray pump holder 110 may be adjusted with respect to the reference platform 104 to vary the angle of the spray axis 136 with respect to the working surface.

Figure 6A:
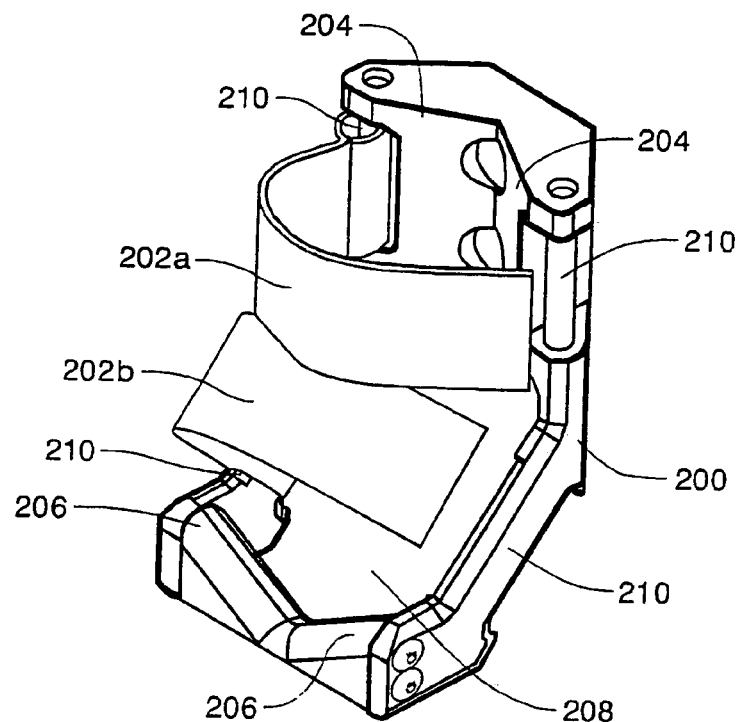
FIG. 6A shows a perspective view of an MDI spray pump holder for the embodiment of FIG. 5A.
Figure 6B:
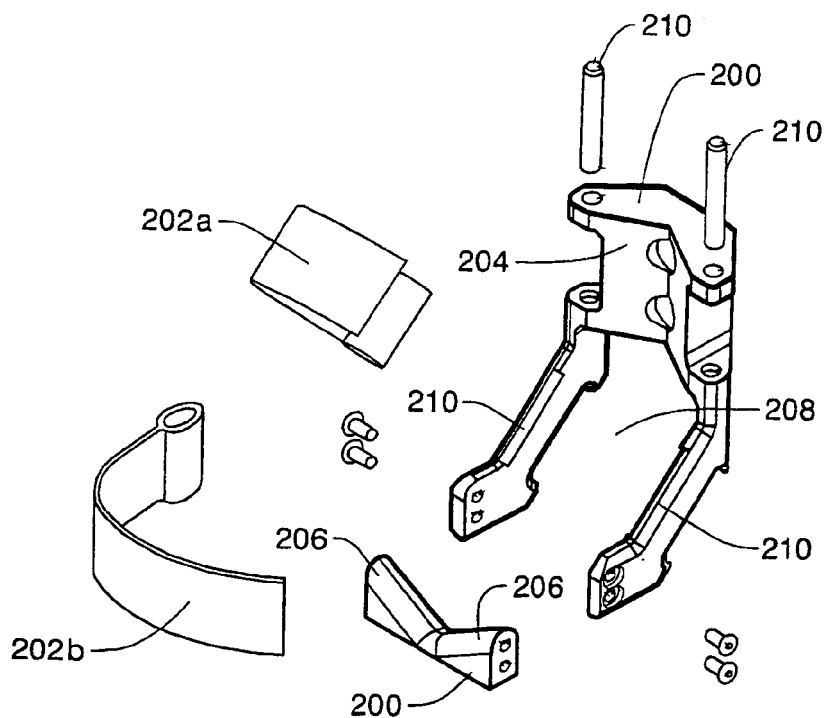
FIG. 6B shows an exploded view of the MDI spray pump holder of FIG. 6A.
Figure 6C:
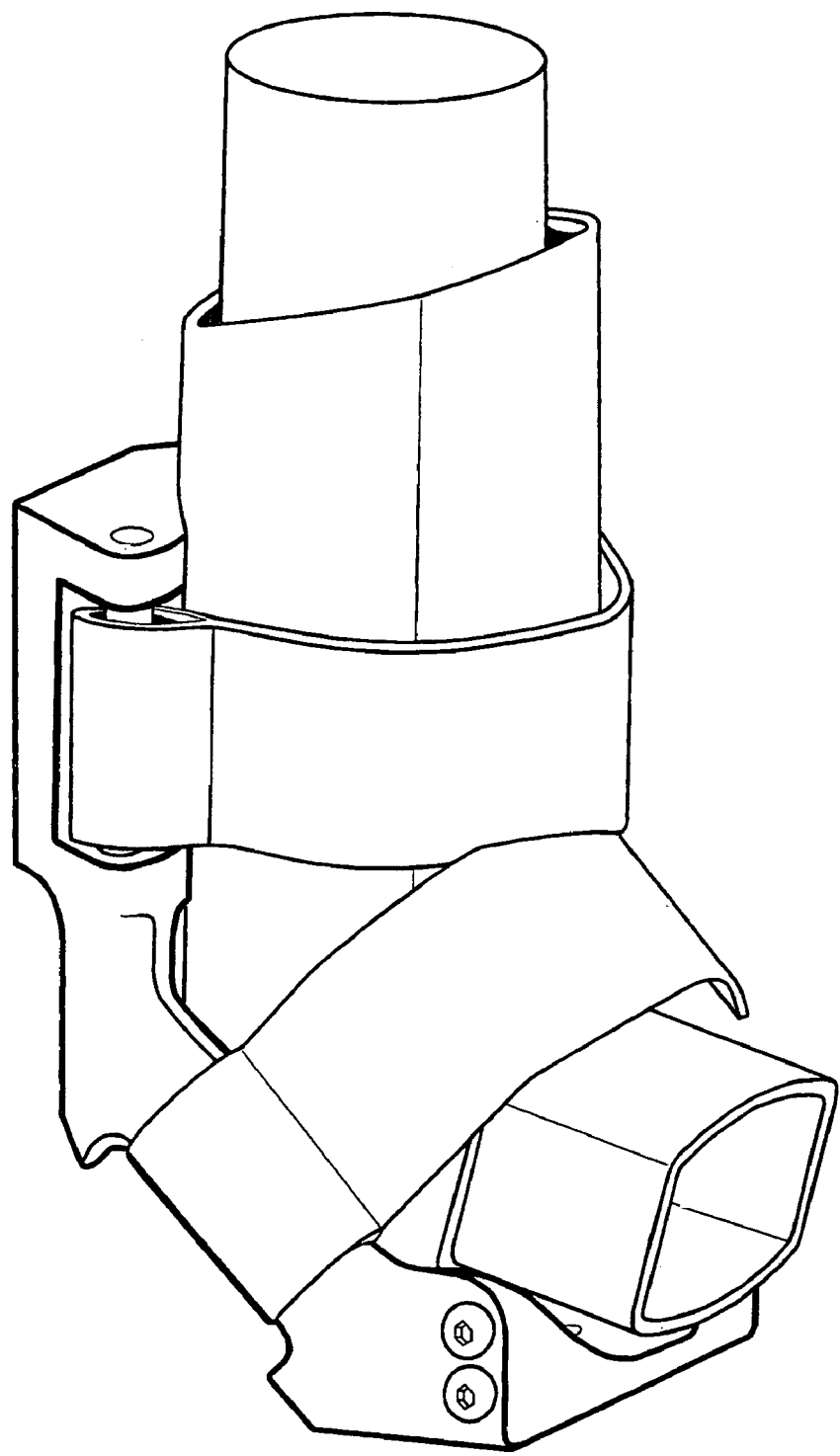
FIG. 6C shows the spray pump holder securing the MDI spray pump assembly of FIG. 6A.

A perspective view of the spray pump holder 110 for the embodiment of FIGS. 5A and 5B is shown in FIG. 6A. An exploded view of the spray pump holder of FIG. 6A is shown in FIG. 6B. FIG. 6C shows the spray pump holder securing the MDI spray pump assembly of FIG. 6A. The spray pump holder 110 for this embodiment includes a bracket 200 for supporting the MDI spray pump assembly and at least one securing strap 202 for securing the spray pump assembly against the bracket 200. The bracket 200 includes a first engaging surface 204 for retaining the back surface of the spray pump assembly, and a second engaging surface 206 for engaging the bottom surface of the spray pump assembly. In one embodiment, the first engaging surface is substantially orthogonal to the second engaging surface 206, so as to be compatible for retaining substantially orthogonal surfaces on an MDI spray pump assembly. In other embodiments, the first engaging surface 204 and the second engaging surface 206 are characterized by a V-shaped surface so as to readily retain arcuate surfaces of the spray pump assembly. In one embodiment, the bracket further includes an aperture 208 between the first engaging surface 204 and the second engaging surface 206. The aperture 208 accommodates a "heel" portion of the MDI spray pump assembly. The embodiment shown in FIGS. 6A and 6B includes two securing straps 202; an upper securing strap 202a and a lower securing strap 202b. In operation, the upper securing strap 202a wraps around the upper portion of the MDI spray pump assembly to secure the back surface of the MDI spray pump assembly to the first engaging surface 204. The lower securing strap 202b wraps around the lower portion of the MDI spray pump assembly to secure the bottom surface to the second engaging surface 206, with the heel of the MDI spray pump assembly through the aperture 208. The bracket 200 further includes a first pair of anchors 210 for the upper securing strap 202a and a second pair of anchors 210 for the lower securing strap 202b. For each securing strap 202, one end is fixedly attached to one of the anchors 210, and the other end is removably attached to the other anchor 210. In one embodiment, the removably attached end of the securing strap 202 loops around the anchor and removably attaches to itself via Velcro or other similar securing mechanism. Other embodiments may secure the MDI spray pump assembly to the bracket 200 using a latching configuration similar to a "ski-boot" securing mechanism well known in the art.

Figure 7A:
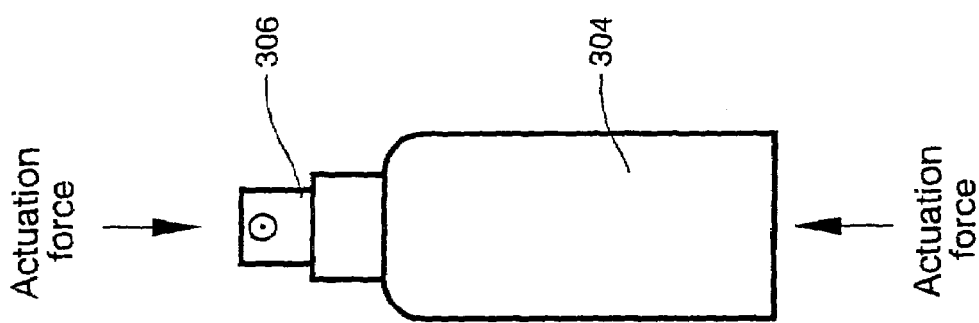
FIG. 7A illustrates one example of an oral spray pump assembly.
Figure 7B:
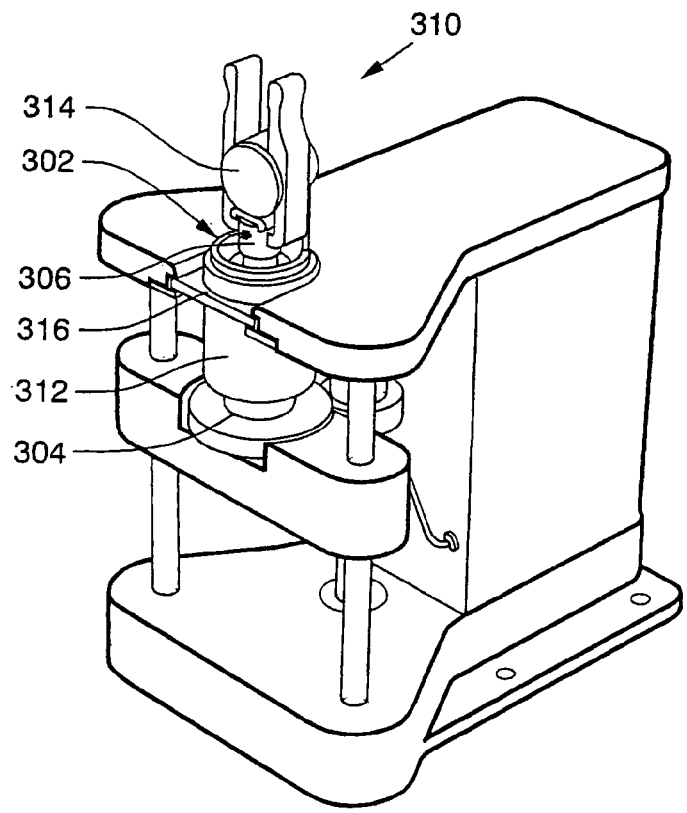
FIG. 7B shows a perspective view of an alternate spray pump holder assembly secured to the oral spray pump assembly of FIG. 7A; and, FIG. 7C shows an exploded view of the alternate spray pump holder assembly of FIG. 7B.
Figure 7C:
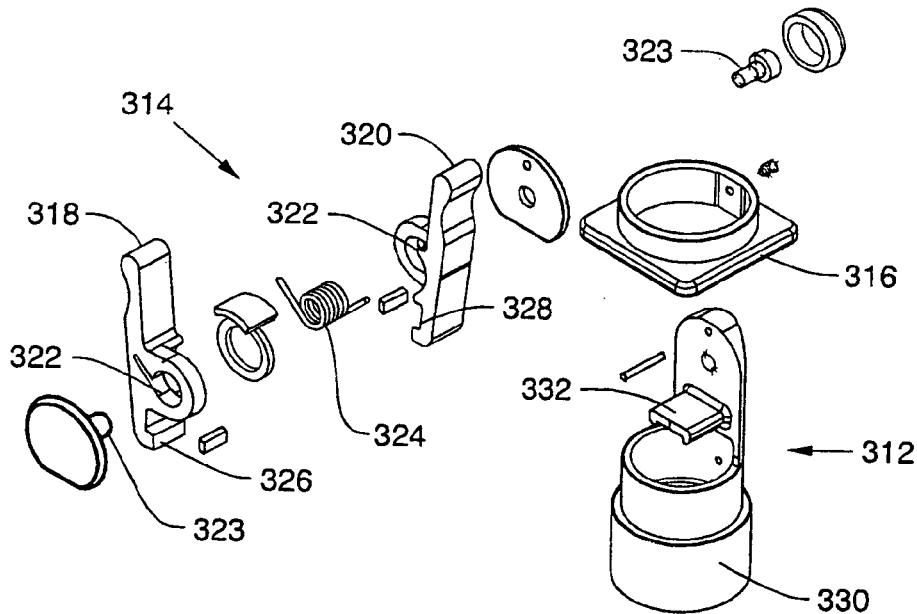

In one embodiment of the actuator system 100 shown in FIG. 3A, an alternate spray pump holder assembly 310 may be used to actuate an oral spray pump assembly. FIG. 7A illustrates one example of such an oral spray pump assembly 302, including a reservoir component 304 and a pump/nozzle component 306. FIG. 7B shows a perspective view of the alternate spray pump holder assembly 310 secured to an oral spray pump assembly 302 and mounted to the actuator of FIG. 3A. FIG. 7C shows an exploded view of the alternate spray pump bolder assembly 310 of FIG. 7B. The assembly 310 includes a base 312 and a clamping assembly 314. The clamping assembly 314 is a spring-loaded "clothespin" type mechanism that grasps the top of the pump/nozzle component 306. The clamping assembly 314 includes a first lever 318 and a second lever 320 pivotally attached at a pivot point 322 via a pivot axle 323. A spring 324 is attached to the first lever 318 and the second lever 320 so as to force a first end 326 of the first lever 318 and a first end 328 of the second lever 320 together, thereby grasping the pump/nozzle component 306. The base 312 includes a housing member 330 and a square body 316. The housing member 330 includes a stop tab 332 against which the top of the pump/nozzle component 306 rests. The stop tab 332 applies resisting force to the top of the pump/nozzle component 306 as the spray pump assembly 302 is actuated. The clamping assembly 314 is attached to the base 312, and the base 312 is removably attached to the reference platform 104 of the actuator system. The base 312 includes a square body 316 that is inserted into the mating grooves 168 of the reference platform.

The core elements the actuating system described herein can not only be used to actuate nasal and oral spray pump assemblies and MDI spray pump assemblies, but rather they should be considered as forming a high precision, position controlled compression apparatus that can be used in a variety of automated actuation applications. Examples of other applications may include, but are not limited to: automated actuation of nasal syringes; testing of automotive fuel injectors; robotic actuation of industrial nozzles; and/or actuation of cosmetic spray pumps.

A user manual related to a nasal spray pump actuator embodiment is included as Appendix A of U.S. application Ser. No. 10/176,930. A user manual related to an MDI spray pump actuator embodiment is included as Appendix B of U.S. application Ser. No. 10/176,930.

The invention may be embodied in other specific forms without departing from the spirit or essential characteristics thereof. The present embodiments are therefore to be considered in respects as illustrative and not restrictive, the scope of the invention being indicated by the appended claims rather than by the foregoing description, and all changes which come within the meaning and range of the equivalency of the claims are therefore intended to be embraced therein.

What is claimed is:

1. A system for actuating a spray pump assembly, the system comprising:
    a motor component for receiving a power input and a control input and producing a rotary drive output therefrom;
    a drive transmission component for receiving the rotary drive output and producing a linear drive output therefrom;
    a spray pump holder component for removably securing the spray pump assembly;
    a force coupler for coupling the linear drive output to the spray pump mechanism, so as to apply a force to the spray pump mechanism;
    a force transducer for producing a force signal proportional to the force applied to the spray pump mechanism; and
    a system controller for receiving a set of test inputs including (i) the force signal, (ii) one or more feedback signals from the motor component, and (iii) user input corresponding to spray pump test parameters, and providing the control input to the motor component as a predetermined function of the set of test inputs;
    wherein the system is operative to actuate the spray pump mechanism according to an actuation profile defined by the set of test inputs.

2. The system of claim 1 wherein the spray pump holder comprises:
    (i) a clamp having an aperture disposed about a central axis, and a plurality of fingers disposed about the perimeter of the aperture and extending out from the clamp parallel to the central axis;
    (ii) a compression member removably attached to the clamp;
    wherein the pump/nozzle component is inserted into the aperture along the central axis, and the compression member, when attached to the clamp, compresses the plurality of fingers against the pump/nozzle component so as to secure the pump/nozzle component to the clamp.

3. The system of claim 2 wherein the clamp consists of a low friction material.

4. The system of claim 3 wherein the low friction material is Teflon.

5. The system of claim 2 wherein the compression member is constructed and arranged so as to variably compress the plurality of fingers against the pump/nozzle component.

6. The system of claim 2 wherein the clamp and the compression member include mating threads, such that the compression member screws into the clamp and drives the fingers toward the central axis.

7. The system of claim 2 wherein the compression member consists of anodized aluminum.

8. The system of claim 2 further including an annular insert disposed about the central axis, between the fingers and the central axis, wherein the pump/nozzle component is inserted through the annular insert and the fingers compress the annular insert against the pump/nozzle component.

9. The system of claim 2 wherein each of the fingers is characterized by a triangular cross section in a plane perpendicular to the central axis.

10. The system of claim 2 wherein the clamp is characterized by a substantially square body disposed within a plane perpendicular to the central axis.

11. The system of claim 10 wherein opposite sides of the square body slide into corresponding grooves in a reference platform.

12. The system of claim 1 wherein the spray pump holder comprises:
    (i) a bracket for supporting the spray pump assembly, and
    (ii) at least one securing strap for removably securing the spray pump assembly against the bracket.

13. The system of claim 12 wherein the bracket includes a first cradle member having a first engaging surface for retaining a first surface of the reservoir component, and a second cradle member having a second engaging surface for retaining a second surface of the reservoir component.

14. The system of claim 13 wherein the first engaging surface is substantially orthogonal to the second engaging surface.

15. The system of claim 13 wherein the first engaging surface includes a V-shaped surface, so that the first engaging surface contacts a reservoir component having an arcuate exterior surface at two locations.

16. The system of claim 13 wherein the second engaging surface includes a V-shaped surface, so that the second engaging surface contacts a reservoir component having an arcuate exterior surface at two locations.

17. The system of claim 13 wherein the bracket further includes an aperture, disposed between the first cradle member and the second cradle member, for accommodating a heel portion of the spray pump assembly.

18. The system of claim 12 further including a first securing strap and a second securing strap, wherein the first securing strap secures the spray pump assembly against the first cradle member, and the second securing strap secures the heel portion of the spray pump assembly into the aperture and against the second cradle member.

19. The system of claim 12 wherein a first end of the at least one securing strap is fixedly attached to a first anchor on the bracket, and a second end of the at least one securing strap is removably attached to a second anchor on the bracket.

20. The system of claim 19 wherein the second end of the at least one securing strap loops around the second anchor removably attaches to a distal portion of the securing strap.

21. The system of claim 1 wherein the spray pump holder comprises:
    (i) a base including a body member, and a housing member having a stop tab; and
    (ii) a clamping assembly including a first lever and a second lever pivotally attached at a pivot point about a pivot axle, and a spring attached to the first lever and the second lever so as to force together a first end of the first lever and a first end of the second lever;
    wherein the stop tab provides a platform against which a pump/nozzle component of a spray pump assembly presses, and the pump/nozzle component is secured between the first end of the first lever and a first end of the second lever.

22. The system of claim 21 wherein the body member is characterized by a square body, and opposite sides of the square body slide into corresponding grooves in a reference platform.

23. A method of actuating a spray pump assembly including a reservoir component and a pump/nozzle component, via an actuator system including a rotary motor driving a linear screw rail assembly, thereby applying a force to the spray pump assembly, the method comprising:
   removably securing the spray pump assembly to a spray pump holder component;
   determining (i) a quiescent position of the spray pump, and (ii) a fully actuated position of the spray pump assembly;
   generating an actuation profile as a predetermined function of the quiescent position, the fully actuated position, and user input corresponding to spray pump test parameters; and
   actuating the spray pump according to the actuation profile wherein determining the quiescent position of the spray pump further includes (i) measuring an amount of force applied to the spay pump assembly, (ii) advancing the linear screw rail assembly until the amount of force applied to the spray pump assembly exceeds a first predetermined value and (iii) recording a position of the linear screw rail assembly when the amount of force applied to the spray pump assembly exceeds the first predetermined value.

24. A method according to claim 23, wherein determining the fully actuated position of the spray pump assembly further includes (i) continuing to advance the linear screw rail assembly until the amount of force applied to the spray pump assembly exceeds a second predetermined value, and (ii) recording a position of the linear screw rail assembly when the amount of force applied to the spray pump assembly exceeds the second predetermined value.

* * * * *